US005906580A

United States Patent [19]

Kline-Schoder et al.

[11] Patent Number: 5,906,580

[45] Date of Patent: May 25, 1999

[54] ULTRASOUND SYSTEM AND METHOD OF ADMINISTERING ULTRASOUND INCLUDING A PLURALITY OF MULTI-LAYER TRANSDUCER ELEMENTS

[75] Inventors: Robert Kline-Schoder, Norwich; David Kynor, Sharon, both of Vt.; Shinzo Onishi, Lebanon, N.H.

[73] Assignee: Creare Inc., Hanover, N.H.

[21] Appl. No.: 08/851,143

[22] Filed: May 5, 1997

[51] Int. Cl.[6] .................... A61B 8/00

[52] U.S. Cl. .................... 600/459; 600/437

[58] Field of Search .................... 600/447, 459, 600/443, 439, 467, 463; 128/903

[56] References Cited

U.S. PATENT DOCUMENTS

| | | | |
|---|---|---|---|
| 4,350,916 | 9/1982 | August et al. | 310/313 |
| 4,509,524 | 4/1985 | Miwa | 600/443 |
| 4,633,122 | 12/1986 | Radice | 310/339 |
| 4,734,044 | 3/1988 | Radice | 439/78 |
| 4,769,571 | 9/1988 | Habeger, Jr. et al. | 310/334 |
| 4,841,977 | 6/1989 | Griffith et al. | 600/439 |
| 5,311,095 | 5/1994 | Smith et al. | 310/334 |
| 5,329,496 | 7/1994 | Smith | 128/661.01 |
| 5,381,385 | 1/1995 | Greenstein | 367/140 |
| 5,458,140 | 10/1995 | Eppstein et al. | 600/573 |
| 5,493,541 | 2/1996 | Snyder | 367/155 |
| 5,530,683 | 6/1996 | Lindberg | 367/164 |
| 5,548,564 | 8/1996 | Smith | 367/140 |
| 5,601,526 | 2/1997 | Chapelon et al. | 601/3 |
| 5,603,323 | 2/1997 | Pflugrath et al. | 128/903 |
| 5,605,154 | 2/1997 | Ries et al. | 128/660.08 |
| 5,744,898 | 4/1998 | Smith et al. | 310/334 |

*Primary Examiner*—Francis J. Jaworski
*Assistant Examiner*—Ali M. Imam
*Attorney, Agent, or Firm*—Downs Rachlin & Martin, PLLC

[57] ABSTRACT

An ultrasonic imaging system capable of transmitting and receiving ultrasound over a wide frequency range, i.e., 500 KHz–300 MHz. Ultrasound may be transmitted from a single transducer array at multiple frequencies simultaneously or sequentially via separate, acoustically isolated transducer elements, each having a unique resonant frequency. Signal-to-noise ratio may be enhanced through use of multiple piezoelectric layer transmit transducer elements and single piezoelectric layer receive transducer elements, both on a single transducer array. Aspect ratios approaching unity for transducer elements of the array may be obtained, which can be used to reduce grating lobes. Sparsely populated transducer arrays are included in the imaging system. Methods of ultrasound imaging and ultrasound therapy obtainable with the present imaging system are included in the invention.

60 Claims, 3 Drawing Sheets

ULTRASOUND SYSTEM AND METHOD OF ADMINISTERING ULTRASOUND INCLUDING A PLURALITY OF MULTI-LAYER TRANSDUCER ELEMENTS

FIELD OF THE INVENTION

The present invention relates to ultrasonic imaging systems and methods of administering ultrasound, and more particularly to ultrasonic imaging systems for, and methods of, administering ultrasound at frequencies ranging from 500 KHz to 300 MHz.

BACKGROUND OF THE INVENTION

New areas of medical study and new clinical applications involving the use of 500 KHz–300 MHz frequency ultrasound imaging are constantly being developed. Ultrasound images made at the high end of this frequency range have spatial resolutions that approach the wavelength of the ultrasound energy, e.g., 20 microns for a 75 MHz ultrasound signal in water. Initial clinical applications of high frequency ultrasound include imaging the eye, the vasculature, the skin, and cartilage. Such imaging may be used, for example, to determine the vertical growth phase of skin cancers, to distinguish between cancerous tissue and fat in the breast, and to determine quantitative information about the structure of atherosclerotic plaque in arteries.

Future improvements in ultrasound image quality will require the fabrication of ultrasonic transducer arrays using designs and fabrication techniques not heretofore available. More particularly, transducer arrays manufactured with current transducer fabrication technology have limited spatial resolution, restricted scan slice thickness, inadequate phase correction capability, and primitive beam steering for volumetric scanning. To overcome these limitations, the next generation of ultrasonic transducer arrays will need to be multi-dimensional and operate over a broad range of frequencies.

Ultrasound imaging arrays having a 2-D (N×M) configuration are the subject of much research and development due to their potential for overcoming some of the above-described limitations of known one-dimensional (N×1) linear arrays. Unfortunately, rapid development and commercialization of 2-D ultrasound imaging arrays has been hampered by difficulties in fabricating transducer elements with small dimensions and low electrical impedance.

Once 2-D ultrasonic imaging arrays having improved resonant frequency, sensitivity and other operating characteristics are developed, it is anticipated a number of ultrasound applications will become available. First, focusing could be performed in an elevation plane that is perpendicular to the primary imaging plane at slice thicknesses and image resolutions not currently available. Second, cross axis phase aberration caused by differences in ultrasonic propagation velocity through different tissue types could be corrected through the use of 2-D imaging arrays. Third, 2-D arrays with improved sensitivity and resolution will allow true volumetric imaging of structures that are too small to be imaged with current technology.

Another area of current interest, high-intensity focused ultrasound (HIFU), has significant potential for use in therapeutic ultrasound applications including noninvasive myocardial ablation, drug delivery, drug activation, ultrasound surgery and hyperthermia cancer therapy. Ideally, HIFU therapies would be performed while simultaneously viewing the area being treated. For example, for therapy, high power sound bursts are delivered at one frequency, while for imaging, a different frequency may be desirable to provide images with sufficient resolution.

Unfortunately, known ultrasonic imaging systems do not typically permit such dual application of ultrasound with a single transducer array. Instead, with current systems, the body region to be treated is generally imaged with a first transducer, and then the HIFU therapy is administered with a second transducer. Introduction of an ultrasound transducer into certain body regions can be a relatively lengthy, e.g., 45 minutes, and risky procedure. Also, appropriate placement of the transducer delivering the HIFU therapy is a challenge given the absence of contemporaneous imaging information.

In an attempt to address this limitation with known ultrasonic imaging systems, experiments have been conducted using broadband ultrasonic transducers, i.e., ceramic and composite-based transducers having an upper frequency that is about 1.6 times the center frequency and a lower frequency that is about 0.4 times the center frequency. By controlling the frequency content of the drive signal, the transducer can be operated to transmit and receive ultrasound near the opposite ends of the transducer's frequency range. However, broadband ultrasonic transducers operated in this manner have a serious shortcoming due to different characteristics of therapy and imaging ultrasound transducers. A sharp resonance is required for improved efficiency for therapy, while a broad bandwidth is required for effective imaging. In addition, in some circumstances it is desirable to provide ultrasonic energy at two frequencies that are spaced farther apart than is achievable with known broadband transducers.

Sheljaskov et al., in the article *A Phased Array Antenna for Simultaneous HIFU Therapy and Sonography*, Proceedings of the 1996 Ultrasound Synopsium, pages 1527–1530, describe an ultrasonic transducer capable of generating ultrasonic energy with the same transducer at 1.7 MHz and 5.5 MHz. The transducer features two piezoceramic layers stacked one on top of the other, and one matching layer. One of the piezoelectric layers is divided into three separately wired sections. The piezoceramic layer divided into three separate sections may be operated independently of the other layer to produce the 5.5 MHz signal. The 1.7 MHz signal is created by operating the entire transducer as a single unit. Thus, the separate piezoelectric sections of the transducer necessarily acoustically communicate with each other. The transducer apparently cannot be operated to provide the 1.7 MHz signal at exactly the same time it is providing the 5.5 MHz signal because the same piezoelectric ceramic is required to produce both the high and low frequency ultrasonic energy. Thus, when Sheljaskov et al. indicate their transducer provides both signals "simultaneously," it is believed they use this term loosely. In addition, it is believed this transducer faces the same limitations as other prior art broadband transducers described above, i.e., non-optimum design for two mutually exclusive uses.

Thus, a need clearly exists for an ultrasonic imaging system for providing multiple frequencies of ultrasonic energy at frequencies higher than those achievable with known imaging systems. In addition, certain ultrasound applications require higher signal-to-noise ratios, and hence resolutions, than are achievable with known dual-frequency imaging systems.

As used herein, the term "1-D array" refers to an array having (N×1) discrete transducer elements, the term "2-D array" refers to an array having (N×M) discrete transducer elements where N and M are equal or nearly equal in number, and the term “1.5-D array” refers to an array having (N×M) discrete transducer elements where >>M, e.g., where N=128 and M=3.

SUMMARY OF THE INVENTION

The present invention is an ultrasonic imaging system comprising a source for providing a first signal and a transducer array connected to the source for providing ultrasonic energy in response to the first signal. The ultrasonic energy provided by the transducer array has a frequency greater than 5 MHz and each transducer array element has an electrical impedance of less than 100 Ohms. The system also includes a processor, user controls and a display.

Another aspect of the invention is an ultrasonic imaging system comprising a source for providing first and second signals and a transducer array connected to the source. The array includes a plurality of first transducer elements for providing ultrasonic energy at a first resonant frequency in response to the first signal and a plurality of second transducer elements for providing ultrasonic energy at a second resonant frequency in response to the second signal. The plurality of first transducer elements is acoustically isolated from the plurality of second transducer elements.

Yet another aspect of the invention is a method of administering ultrasound comprising the steps of (a) providing an ultrasound transducer array, (b) providing a first ultrasound signal from the transducer array, the first ultrasound signal having a first resonant frequency, and (c) providing a second ultrasound signal from said transducer array, the second ultrasound signal having a second resonant frequency that is different than the first resonant frequency. One of the first and second ultrasound signals has a resonant frequency greater than 5 MHz.

Still another aspect of the invention is a method of administering ultrasound comprising the steps of (a) providing an ultrasound transducer array, (b) providing a first ultrasound signal from the transducer array, the first ultrasound signal having a first resonant frequency, and (c) receiving a second ultrasound signal with the transducer array, the second ultrasound signal having a second resonant frequency that is different than said first resonant frequency. One of the first and second ultrasound signals has a resonant frequency greater than 5 MHz.

DETAILED DESCRIPTION OF THE INVENTION

The present invention is an ultrasonic imaging system and a method of administering ultrasound. The ultrasonic imaging system is described immediately below, and then a description of methods of administering ultrasound using the system follows.

1. System

Figure 1:
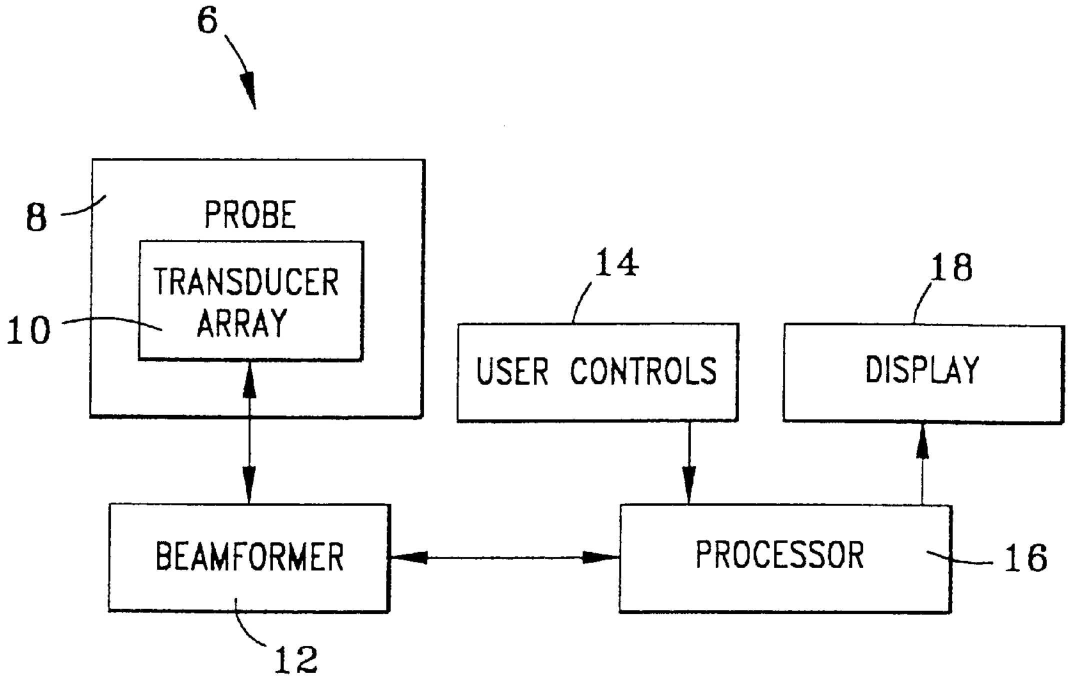
FIG. 1 is a block diagram of the ultrasonic imaging system of the present invention.

Referring to FIG. 1, ultrasonic imaging system 6 includes a probe 8 having a transducer array 10 for converting electrical energy into ultrasound energy and vice versa. Although one probe 8 is illustrated in FIG. 1, system 6 may include multiple probes. Transducer array 10 is an important aspect of the present invention, and is described in more detail below following the description of other components of system 6.

The size and shape of probe 8 depends upon its intended application. For example, when probe 8 is intended for use in non-invasive scanning from the surface of a body, the probe may have a flat face (not shown) or may be contoured to match a particular part of the body (e.g., designed to conform to the shape of the breast). Alternatively, probe 8 may have a flexible face (not shown) that conforms to specific parts of the body as it is move across such parts. Probe 8 may also be incorporated in a catheter, endoscope or laparoscope (none shown) used for ultrasound applications from the interior of the body. In addition, probe 8 may be incorporated in an intracavity probe (not shown) that is inserted into a body cavity (e.g., the esophagus or vagina). Also, probe 8 may be deposited onto, or form part of, a tool (not shown) intended for a specific use such as a cardiac catheter. In many cases, the size and configuration of transducer array 10 will need to conform to these alternative configurations of probe 8, as described in more detail below in connection with the description of the array.

As is known in the art, probe 8 may include acoustic lenses (not shown) to focus ultrasound energy, and a backing layer (not shown) that substantially reduces inter-element cross-talk and reverberation of transducer array 10. In addition, probe 8 may include a matching layer (not shown in FIG. 1) for matching the acoustical impedance of transducer array 10 with the acoustical impedance of body fluids or body parts in connection with which ultrasonic imaging system is used. Probe 8 may also include preamplifiers (not shown) for amplifying the electrical output of transducer elements (not shown in FIG. 1) of array 10.

Ultrasonic imaging system 6 also includes a beamformer 12 connected to transducer array 10. Beamformer 12 provides the electrical waveforms that drive individual transducer elements (described below) of transducer array 10. As is known, beamformer 12 generates a variety of waveforms ranging from short impulses used for detailed anatomical imaging to longer pulses that are used for flow imaging or gross anatomic imaging. The selection of the electrical waveform generated by beamformer 12 varies with the intended application, as those skilled in the art will appreciate.

Beamformer 12 also receives the electrical output signals generated by individual transducer elements upon receipt of ultrasonic energy reflected from a target. Beamformer 12 electronically focuses and steers the beam of acoustic energy by delaying the signals from different transducer elements before adding them together. The goal of beamforming is to optimize the resulting image so that each display pixel, or voxel in the case of 3-D imaging, is representative of a small region of the imaging volume.

Ultrasonic imaging system 6 includes user controls 14. The latter is used to provide system 6 with information concerning frequency, pulse duration, pulse amplitude, probe shape, focal region, focal depth and imaging mode (e.g., Doppler mode, A-mode, B-mode or C-mode, etc.).

Ultrasonic imaging system 6 further comprises processor 16. The latter controls the overall operation of system 6. Processor 16 is connected to user controls 14, and responds to inputs provided via such controls. Processor 16 is also connected to beamformer 12, and controls the operation of the latter. Processor 16 converts the composite beamformed signal provided by beamformer 12 into a brightness image and, in the case of Doppler flow imaging, an audio signal representing measured flow rates. Processor 16 also interpolates and rescales the brightness image prior to display and performs color and gray-scale mapping.

Finally, ultrasonic imaging system 6 includes display 18 for displaying a brightness image for interpretation by the user. Display 18 is connected to processor 16 and generates the brightness image based on information in the output signal of the display processor.

Beamformer 12, user controls 14, processor 16 and display 18 are all conventional components of the type used in known imaging systems. For a more detailed description of these components and the functions they perform, attention is directed to the book entitled *Ultrasonic Signal Processing*, edited by A. Alippi, World Scientific Publishing Company, Incorporated, River Edge, N.J. Also, U.S. Pat. No. 5,603,323 to Pflugrath et al., incorporated herein by reference, describes known components 12–18 of imaging system 6.

As will be apparent following a more detailed description of transducer array 10, provided below, ultrasonic imaging system 6 may require several fairly simple modifications. First, the number of input channels in and output channels from beamformer 12 may need to be increased. Second, the voltage and impedance of the drive signal for transducer array 10 provided by beamformer 12 may need to be decreased. Third, it may be desirable to modify display information provided by processor 16 to display 18 so that multiple images may be displayed simultaneously, e.g., by split screen images.

Ultrasonic transducer array 10 is described in U.S. patent application Ser. No. 08/841,797, filed concurrently herewith, to Robert Kline-Schoder and Shinzo Onishi, entitled "Multilayer Ultrasonic Transducer Array" (the "Kline-Schoder Application"), which application is incorporated herein by reference. Transducer array 10 is intended to represent all embodiments of the transducer arrays described in the Kline-Schoder Application, i.e., arrays 20, 120, 220, 320, 420 and 520. Although brief description of these arrays is provided below, attention is directed to the Kline-Schoder Application for a more detailed description of these arrays.

Figure 2:
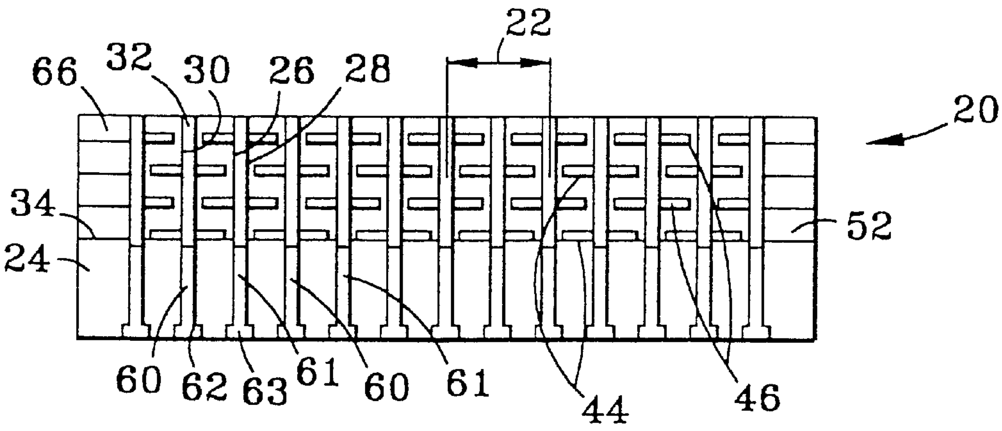
FIG. 2 is a cross section of one embodiment of the transducer array of the imaging system illustrated in FIG. 1.

Referring to FIGS. 1 and 2, one embodiment of transducer array 10, identified as transducer array 20 in FIG. 2, comprises a plurality transducer elements 22 positioned on substrate 24. Each element 22 has an associated resonant frequency. Each element 22 is bounded by a pair of kerfs 26 in which connectors 28 are positioned, and is bisected by a kerf 30 in which connectors 32 are positioned. Connectors 28 and 32 are electrically conductive and acoustically isolating. Each element 22 includes electrodes 44 attached to connectors 30 and electrodes 46 attached to connectors 32.

A plurality of piezoelectric layers 52 separate adjacent electrodes 44 and 46. Preferably, although not necessarily, piezoelectric layers 52 are made from PZT. A plurality of kerfs (not shown) comprising barriers (not shown) made from an acoustically and electrically isolating material extend perpendicular to kerfs 26 and 30, and separate adjacent elements 22 in the Z dimension (i.e., the dimension extending into the page in FIG. 2). Connectors 28 are attached via studs 60 to beamformer 12 and connectors 32 are attached to beamformer 12 via studs 61. Studs 60 terminate at pads 62 and studs 61 terminate at pads 63. Ball-grid arrays (or other known high connection count wiring devices) and wiring (neither shown) carry signals from studs 60 and 61 to beamformer 12. Studs 60 carry the positive voltage signal and studs 61 are connected to ground. Attention is directed to the Kline-Schoder Application for a more complete description of transducer array 20. Array 20 may have a 1-D, 1.5-D or 2-D configuration.

Electrical impedance of a multilayer transducer array having X layers is reduced by a factor of $X^2$ compared to a single layer transducer element of similar dimension. Accordingly, the electrical impedance of a transducer, for a given frequency, can be made lower than the electrical impedance of known single layer transducer elements or known multilayer transducer arrays by increasing the number of piezoelectric and electrode layers in transducer array 10. It is desirable to approximately match the electrical impedance of the drive signal provided by beamformer 12 with the electrical impedance of transducer array 10.

An important advantage of the present invention is that the footprint, i.e., length by width dimension, of the elements of multilayer embodiments of transducer array 10, e.g., transducer elements 22 (FIG. 2), or elements 122*c* and 122*d* (FIG. 3), is smaller than that achievable with prior ultrasonic transducer array designs. Accordingly, such embodiments of transducer array 10 may be used in confined-space applications such as catheters and intracavity probes where known transducer arrays will not fit. It is believed the smallest transducer element that can be achieved with prior art multilayer transducer element designs has a minimum width of about 170 microns and minimum length of about 170 to 850 microns. Thus, the minimum width×length area of the smallest known ultrasonic transducer elements is about 0.0289 $mm^2$. By comparison, for elements 22 having a PZT piezoelectric layer 52 and a resonant frequency of 100 MHz, which is easily achievable with the present invention, the width of element 22 is about 8.5 microns, the length is about 8.5 to 42.5 microns, and the width×length area is 72.25 to 361.25 $microns^2$.

Figure 3:
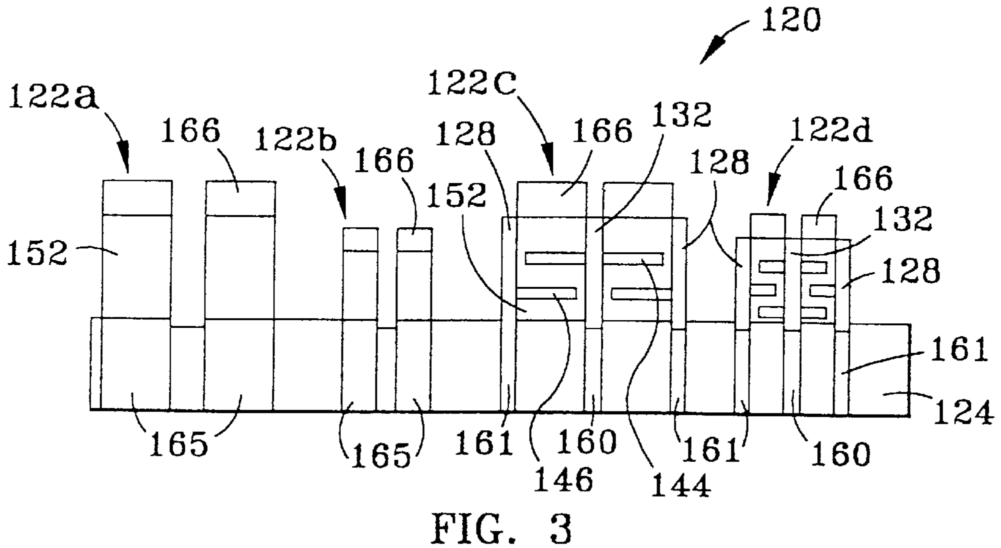
FIG. 3 is a cross section of another embodiment of the transducer array of the imaging system illustrated in FIG. 1, shown in idealized view.

Referring to FIGS. 1–3, another embodiment of transducer array 10 (FIG. 1) is identified in FIG. 3 as transducer array 120. Except as described below and in the Kline-Schoder Application, transducer array 120 (FIG. 3) is identical to transducer array 20 (FIG. 2). Thus, structure in transducer array 120 that is common to array 20 is identically numbered, except that such structure is designated with "100" series reference numerals.

Transducer array 120 differs from array 20 in that it comprises four different types of elements 122, i.e., transducer elements 122*a*, 122*b*, 122*c* and 122*d*. Elements 122*a* and 122*b* have a single piezoelectric layer 152. Elements 122*a* are taller than elements 122*b*, and so have a lower resonant frequency than element 122*b*. Elements 122*c* and 122*d* have multiple piezoelectric layers 152 and associated electrodes 144 and 146. Elements 122*c* are taller than elements 122*d*, and so have a lower resonant frequency than elements 122*d*. Because of their multilayer construction, elements 122*c* and 122*d* have a lower electrical impedance than corresponding elements 122*a* and 122*b*. While transducer array 120 has been described as including four different types of elements 122, the array may include one or any combination of elements 122*a*, 122*b*, 122*c* and 122*d*. Thus, transducer array 120 may comprise elements 122 having two or more different electrical impedances and two or more resonant frequencies. In addition, array 120 may have a 1-D, 1.5-D or 2-D configuration.

Multilayer transducer elements 122*c* and 122*d* include connectors 128 and 132. Connectors 128 are electrically connected to electrodes 146 and connectors 132 are electrically connected to electrodes 144. Metal studs 160 and 161 are connected respectively to connectors 132 and 128. Studs 160 are connected to a positive voltage source and studs 161 are connected to ground, both provided via beamformer 12. Single layer transducer elements 122*a* and 122*b* are electrically connected to a positive voltage source by metal studs 165. Single layer transducer elements 122*a* and 122*b* are connected to ground by a thin conductive foil layer (not shown) positioned on top of the piezoelectric layers 152 of the elements and beneath matching layer 166. The foil layer is connected to ground by way of leads attached to the foil layer adjacent the periphery of array 120. Beamformer 12, which provides the positive voltage source and ground, is connected via ball-grid arrays (or other known high connection count wiring devices) and wiring (neither shown) to studs 160, 161 and 165, and hence to array 120. In 1.5-D and 2-D arrays, adjacent elements 122*a*, 122*b*, 122*c* and 122*d* are separated, as measured along the Z axis (i.e., the dimension extending into the page in FIG. 3) by acoustically and electrically isolating barriers (not shown).

Figure 4:
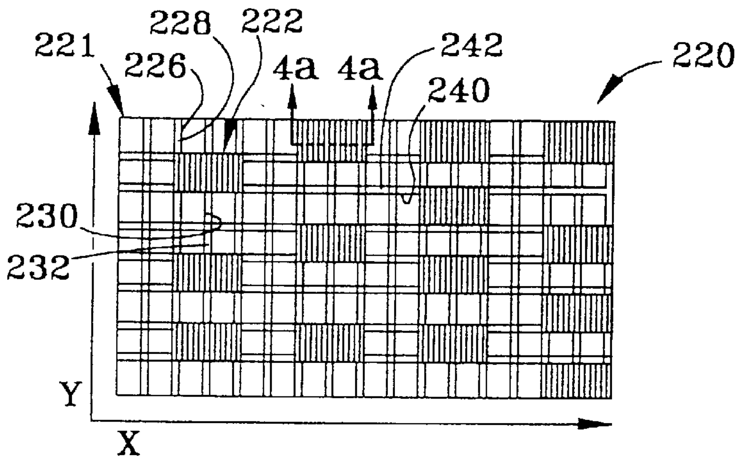
FIG. 4 is a top idealized view of a random sparse array embodiment of the transducer array of the imaging system illustrated in FIG. 1.
Figure 4A:
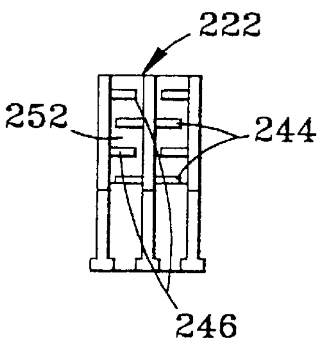
FIG. 4*a* is a partial cross section of a transducer element taken along line 4*a*—4*a* in FIG. 4.

Referring to FIGS. 1 and 4, in another embodiment of transducer array 10, illustrated in FIG. 4 as array 220, a sparse array is provided. In the following description of array 220, structure in the array that is common to array 20 is identically numbered, except that a "200" series designation is used. Sparse array 220 has N×M regions 221 in which transducer elements 222 may be positioned. N refers to the number of regions 221, as measured along the Y axis in FIG. 4 and M refers to the number of regions 221, as measured along the X axis in FIG. 4. In transducer array 220, not all regions 221 contain elements 222. As such, array 220 may be considered a "sparse" array where X(N×M) regions 221 contain elements 222, and X<1. In practice, X ranges from 0.01 to 0.5.

A given element 222 is defined, in part, by kerfs 226 having connectors 228 provided therein, and kerfs 230 having connectors 232 provided therein. Electrodes 244 are electrically connected to connectors 232 and are electrically isolated from connectors 228. Electrodes 246 are electrically connected to connectors 228 and are electrically isolated from connectors 232. Piezoelectric layers 252 separate adjacent electrodes 244 and 246, separate electrodes 244 from connectors 228 and separate electrodes 246 from connectors 232. Kerfs 240 further define elements 222. Kerfs 240 extend perpendicular to kerfs 226 and 228 and have acoustically and electrically isolating barriers 242 provided therein. Regions 221 that do not include an element 222 comprise an electrically and acoustically isolating material of the type used for barriers 242, as described above.

Elements 222 may contain a single piezoelectric layer 252 or may contain multiple piezoelectric layers, as described above relative to transducer 120. To achieve multiple resonant frequencies within array 220, elements 222 having different heights may be provided, as described above relative to elements 122*a–d*.

Figure 5:
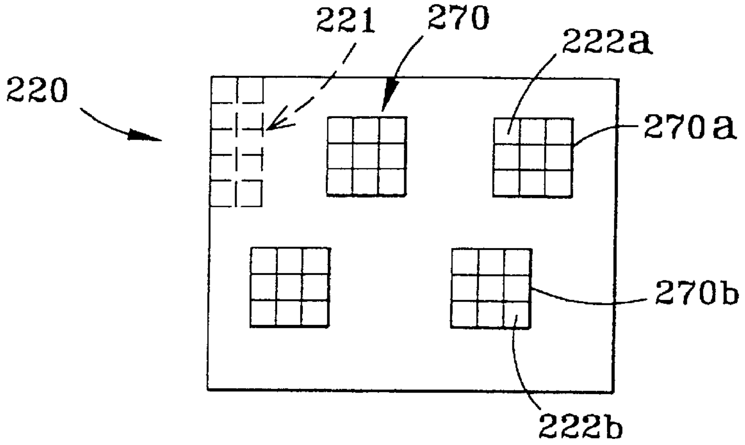
FIG. 5 is a top idealized view of a cluster sparse array embodiment of the transducer array of the imaging system illustrated in FIG. 1.

Referring to FIGS. 1, 4 and 5, elements 222 may be positioned in regions 221 so that no elements are immediately adjacent, as illustrated in FIG. 4. Alternatively, as illustrated in FIG. 5, collections of elements 222 may be provided in clusters 270 of adjacent regions 221, while surrounding regions do not contain any elements. Elements 222 may be designed to transmit and receive ultrasonic pulses, or may be designed to transmit or receive ultrasonic pulses. In the latter case, the construction and configuration of the elements 222 may be optimized for either transmit or receive functions, thereby increasing the sensitivity (i.e., signal-to-noise ratio) of the array. In array 220 illustrated in FIG. 5, clusters 270*a* of adjacent elements 222*a* are optimized to transmit an ultrasonic pulse and clusters 270*b* of adjacent elements 222*b* are optimized to receive an ultrasonic pulse. In this regard, elements 222*a* in cluster 270*a* preferably have multiple piezoelectric layers 252 so as to reduce the electrical impedance of the elements to approximately that of beamformer 12 that drives the elements. Elements 222*b* in cluster 270*b* have a single piezoelectric layer 52 so that their high output impedance can drive high input impedance pre-amplifiers (not shown) located near elements 222*b*. By clustering elements 222*a* and 222*b* in this manner, many of the regions 221 do not contain either of such elements. (In FIG. 5 only several of the regions 221 are illustrated for clarity of illustration. However, regions 221 cover the entire array.)

The various embodiments of transducer array 10, as illustrated in FIGS. 2–5 and described above, feature a planar configuration. As described in more detail in the Kline-Schoder application, transducer array 10 may have curved, i.e., concave or convex, configuration or may have an axial configuration, i.e., a configuration featuring a central axial core with circular or semi-circular transducer elements surrounding the core. These non-planar arrays are identified in the Kline-Schoder Application as transducer arrays 320, 420 and 520. Use of such non-planar arrays is advantageous when, for example, probe 8 has a curved body-contacting face or, in the case of the axial array, when the array is included in a probe intended for intra-cavity applications, e.g., in a catheter or esophagus probe.

2. Methods Of Using The System

A general description of the operation of system 6 is provided immediately below, followed by a detailed description of new ultrasound application methods that may be performed using system 6.

To operate system 6, a user provides input commands via user controls 14 regarding the frequency, duration and other aspects of the ultrasound signals to be generated by probe 8. Processor 16 responds to inputs from user controls 14, processes ultrasonic information and controls the overall operation of system 6.

Ultrasonic energy is transmitted by probe 8 into the target, e.g., a portion of a human body or an integrated circuit, in response to a drive signal from beamformer 12. The latter also receives output signals from probe 8 which the probe generates in response to receipt of ultrasonic energy reflected from the target to which the probe transmitted ultrasonic energy. If more than one probe 8 is used, beamformer 12 also provides control signals for selecting the probe intended to transmit ultrasonic energy. Under the control of processor 14, beamformer 12 processes the ultrasound reflection information contained in the output signal of probe 8.

Processor 14 processes the ultrasound information provided by beamformer 12 to form display information such as an ultrasonic B mode image, Doppler images or spectral information, or other information derived from the ultrasound information. The display information generated by processor 14 is displayed on display 18.

Because transducer array 10 in probe 8 has structure, material thicknesses and other features not present in prior art transducer arrays, new methods of applying ultrasound, including new imaging and therapy methods, may be achieved with system 6. One important aspect of transducer array 10 is that the thicknesses of its piezoelectric layer(s) and electrodes is significantly less than that presently achievable with known transducer array designs and fabrication techniques. Resonant frequency of ultrasonic transducer arrays is proportional to the height of the array elements, e.g., elements 22 in FIG. 2. Because the height of array 10 can be significantly less than that of known arrays due to the thinness of its piezoelectric and electrode layers, array 10 is capable of transmitting ultrasonic energy at frequencies far in excess of those known single ultrasonic transducers or known transducer arrays are capable of transmitting and receiving. Known multilayer transducer arrays are believed to be incapable of generating ultrasonic energy having frequencies in excess of about 5 MHz. Because many portions of the human body and other targets to be imaged have features too small to resolved by ultrasonic energy generated at these frequencies, system 6 opens new opportunities for ultrasonic imaging.

More specifically, system 6 is capable of generating ultrasonic energy at resonant frequencies in the range 500 KHz to 300 MHz. The desired frequency in this range is selected with user controls 14. Based on this input, beamformer 12, under the control of processor 16, provides a voltage drive signal to transducer array 10 having the appropriate sine wave frequency necessary to cause the transducer array to transmit ultrasonic energy of the frequency selected by the user. Reflections of such energy off the target are then processed and represented on display 18, as described above.

System 6 may also be operated to provide two or more frequencies of ultrasonic energy that are spaced farther apart than is typically obtainable with known broadband or other multiple frequency ultrasonic transducers. As noted above, known broadband multiple frequency transducers are restricted in their frequency spread by signal-to-noise constraints and to an upper frequency that is approximately 1.6 times the center frequency, and a lower frequency that is approximately 0.4 times the center frequency. No such limitation exists with system 6. Moreover, the absolute spacing between frequencies of ultrasonic energy that can be produced with known broadband transducers is restricted due to the maximum frequency obtainable with known transducers. More particularly, it is believed known transducers cannot achieve absolute frequency spacing in excess of about 15 Mhz. Thus, with selection of an appropriate transducer array 10, and by appropriate input via user controls 14, the present method involves transmission and/or receipt of ultrasonic energy having a frequency spread broader than the "1.6/0.4" restriction of prior art broadband systems, with an absolute spread in excess of 15 MHz. Indeed, a low center frequency ultrasonic signal of 500 KHz and high resonant frequency ultrasonic signal of 300 MHz is encompassed by the present method. Because the separate transducer elements responsible for generating ultrasonic energy at these disparate frequencies are acoustically isolated from one another (e.g., by connectors 228, 232 and 242 in FIG. 4), high sensitivity and hence image resolution is obtainable with the present method.

Furthermore, the element of transducer array 10, e.g., elements 122*a*, 122*b*, 122*c* and 122*d*, each have a unique resonant or center frequency. Thus, array 10 may have 1, 2, 3 or more resonant frequencies. By contrast, multiple frequency broadband transducers have one resonant frequency. As such, when operated to produce multiple frequencies at least one of the multiple frequencies is not a resonant frequency. Accordingly, sensitivity, and hence image resolution, suffers.

Another aspect of the present invention is operating beamformer 12 so as to generate a drive signal used to drive the transducer array 10, which drive signal has an electrical impedance lower than that achievable with prior art systems for a given frequency. As noted above, because transducer array 10 may have piezoelectric layers, e.g., layer 52 in FIG. 2, that are significantly thinner than those obtainable with prior art multilayer transducer arrays, the electrical impedance of array 10 may be significantly lower than that achievable with prior art imaging systems. Accordingly, the electrical impedance in the drive signal from beamformer can be lower. For example, beamformer 12 may be operated to generate a drive signal having an electrical output impedance of 50 Ohms and a frequency of 5 MHz. It is believed known that multilayer transducer arrays which may be capable of generating ultrasonic energy at 5 MHz have an electrical impedance that is much higher than 100 Ohms. As such, a drive signal of 50 Ohms would create a sufficiently great impedance mismatch that operation of the transducer would be severely compromised. By way of further example, for a transducer array 10 having a resonant frequency of 10 MHz, its associated electrical impedance is 100 Ohms, for an array 10 having a resonant frequency of 15 MHz, its associated electrical impedance is 100 Ohms, and for an array having a resonant frequency of 20 MHz, its associated electrical impedance is 150 Ohms.

As described above, transducer array 10 has a 2-D configuration. This configuration permits system 6 to be used for volumetric (i.e., three-dimensional) imaging. In addition, this configuration permits shaping, focusing and steering of ultrasonic energy transmitted by transducer array 10. These methods of using system 6 are achieved by delivery of drive signals from beamformer 12 to selected transducer elements of array 10, at selected times, so as to achieve these imaging functions. In addition, image focusing and steering may be performed by beamformer 12 using ultrasonic energy reflection information contained in the output signal of transducer array 10. These imaging operations are known in the art.

However, present method differs from the prior art insofar as higher frequencies and superior image resolution is achievable with imaging system 6. Relatedly, thinner scan slice is achievable with the present imaging method than is available with known imaging systems due to the high frequencies of ultrasonic energy obtainable with system 6.

System 6 may be used in the application of ultrasound at multiple frequencies transmitted at the same time. This method of ultrasound application is not believed to be achievable with known multilayer ultrasonic transducer arrays at frequencies and frequency spreads encompassed by the present method. Thus, one cannot enjoy the benefits of lower electrical impedance associated with multilayer transducer arrays without using two or more transducer arrays when it is desired to transmit multiple frequencies of ultrasound simultaneously. In many circumstances use of multiple transducer arrays for simultaneous application of ultrasound is disadvantageous.

Nor are known ultrasonic transducers that can generate multiple frequencies of ultrasound capable of doing so at sensitivities achievable with system 6. Thus, another aspect of the present method is transmitting and receiving ultrasonic energy at a signal-to-noise ratio that is higher than that achievable with known multiple frequency ultrasonic transducers. Signal-to-noise ratio is optimized with the present invention using the embodiments of transducer array 10 illustrated in FIG. 3 and identified as array 120 or FIG. 5 and identified as array 220. As described above, such optimization is achieved using multilayer transducer array elements 122*c* and 122*d* to transmit ultrasonic energy and single layer transducer array elements 122*a* and 122*b* to receive reflection of such ultrasonic energy from the target. With array 220, element clusters 270*a* transmit ultrasonic energy and element clusters 270*b* receive ultrasonic energy. Indeed, with the present invention, at a given pair of frequencies, the signal-to-noise ratio of transducer array 10 may be 10–20 dB higher than that achievable with known multiple frequency transducer arrays.

Figure 6:
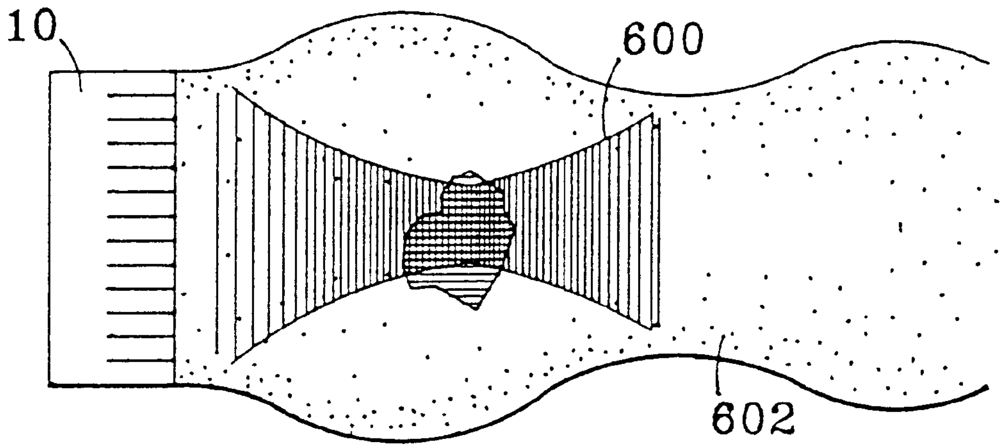
FIG. 6 is an idealized view of the transducer array of the imaging system, an adjacent target, a portion of the target, and a low frequency beam of ultrasonic energy generated by the transducer array.
Figure 7:
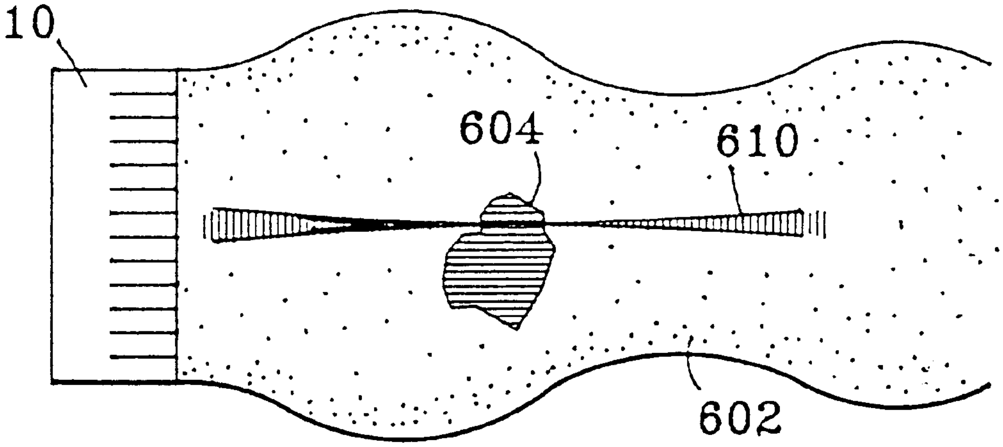
FIG. 7 is the same as FIG. 6, except that a high frequency beam of ultrasonic energy is illustrated.

Referring now to FIGS. 1, 6 and 7, new methods of administering ultrasound that are achievable with system 6 are described below. One aspect of the method of the present invention involves the transmission by transducer array 10 of multiple frequencies of ultrasonic energy. As illustrated in FIG. 6, transducer array 10 is operated to transmit ultrasonic energy beam 600 into target 602 so as to intersect portion 604 of the target. Target 602, for example, may be an internal body organ and portion 604 a lesion on such organ. Alternatively, target 602 may be an integrated circuit chip and portion 604 specific structure, e.g., a stacked capacitor, on the chip. At the same time, or at another time, as desired, transducer array 10 is operated to transmit ultrasonic energy beam 610 into target 602 so as to intersect portion 604.

Beam 600 has a lower frequency than beam 610, and so is broader and intercepts a larger section of portion 604. Typically, beam 600 may be used for gross target imaging, i.e., imaging a relatively large section of the target. Beam 610 has a higher frequency than beam 600, and so is narrower and intercepts a smaller section of portion 604. Beam 610 may be directed based on the information provided by beam 600. Beam 610 may be used for a variety of ultrasound applications, as described below.

In one aspect of the present method, beam 610 may be used for fine target imaging, i.e., imaging a relatively small section of the target. Because of the very high frequencies of ultrasonic energy achievable with transducer array 10, system 6 is capable of resolving details in portion 604 that cannot be resolved with current ultrasound imaging systems, i.e., details as small as 5 microns. An important feature of system 6 is that this fine imaging can be done at the same time as the gross imaging is conducted. This is advantageous because it enables rapid location of portion 604 of target 602.

In another aspect of the present method, when portion 604 is human or animal tissue, beam 610 may be used to provide ultrasonic energy treatment to such tissue. By selection of appropriate frequency for beam 610, via user controls 604, it is possible to ablate, incise or provide heat treatment to tissue with a high degree of control and precision. Such ultrasonic energy treatment may be performed at the same time as system 6 is used to provide gross imaging of the general region of the body where the tissue to be treated is located via beam 600.

The ability to simultaneously image and treat tissue is highly desirable from the standpoint of reducing the time needed to complete the tissue treatment and accuracy of results, both leading to increased patient safety. Perhaps more importantly, the present method of applying multiple frequencies of ultrasonic energy for tissue therapy offers more flexibility and control than with known methods due to the broad frequency spread, high frequencies, and high resolution (due to high transducer sensitivity) available with the present method.

In yet another aspect of the present method, beam 610 may be used for harmonic imaging, i.e., ultrasonic imaging using a contrast agent such as microbubbles. Harmonic imaging involves adding a contrast agent to blood in a targeted organ such as an artery or kidney, and then exposing the organ to ultrasonic energy having a first frequency. Following contact with the contrast agent, harmonics of the first frequency are reflected back to the source of the ultrasonic energy. A transducer capable of receiving the frequencies of the harmonics then provides an output signal containing information and data concerning the flow of blood in the organ being imaged.

Although harmonic imaging is still in its infancy, sufficient experiments have been conducted to appreciate restrictions that existing ultrasonic imaging systems place on this imaging technique. These experiments indicate it is difficult with known imaging systems to achieve the desired spatial resolution and to adequately reject ultrasonic energy resulting from reflection of the first frequency from structure not containing the contrast agent. In particular, to achieve the bandwidth in a single transducer needed to transmit ultrasonic energy at the first frequency and receive ultrasonic energy at harmonics thereof, it is believed known imaging systems cannot provide the desired spatial resolution and cannot adequately reject reflected ultrasonic energy of the first frequency.

The present method of harmonic imaging is identical to known harmonic imaging methods in that it involves the addition of a contrast agent, e.g., microbubbles, in a dilute concentration of about 0.01 to 0.1 ml/kg to a blood-containing organ such as an artery. Also like known methods, the present method of harmonic imaging involves the transmission of ultrasonic energy at a first frequency, i.e., beam 600, where portion 604 is a blood-containing organ.

The present method differs from known harmonic imaging methods in the way reflected harmonics are processed. With the present method, a multiple frequency transducer array, such as array 120 is used to receive harmonics of beam 600 reflected from the contrast agent in portion 604. For example, with reference to FIG. 3, transducer elements 122*c* may used to transmit beam 600 at a first frequency, and transducer elements 122*b* may be used to receive harmonics of beam 600 reflected from the contrast agent in portion 604. Because elements 122*b* and 122*c* are separate, acoustically isolated structures, it is possible to achieve a high contrast, detailed image of blood flow in the tissue being imaged.

Yet another aspect of the present method, is the use of beam 610 for the transdermal transport into, and activation of drugs in, a desired organ or other body region. Ultrasound has been shown to enhance the transdermal transport of a variety of drugs such as testosterone, insulin, progesterone and benzene. Although the mechanisms responsible for this phenomenon are not well documented, it is believed the ultrasound causes micropores in the epidermis to expand allowing the drugs to enter. In addition, evidence suggests the efficacy of drugs is enhanced through application of ultrasound.

In the present method, portion 604 of a organ or other body region into which a drug is to be transported or activated is imaged using beam 600. At the same time, or some time thereafter, beam 610 is transmitted into portion 604. Ultrasonic energy of beam 610 results in transdermal transport or activation of the drug. The specific frequencies and intensities necessary to achieve such transdermal transport and/or activation are believed to vary with the drug and organ or other body portion involved.

Because for transport and activation of certain drugs in certain organs or other body portions ultrasonic energy at higher frequencies than that achievable with known imaging systems may be required, the present method offers great opportunities in this area. The ability to image and perform drug transport and/or activation at the same time using beams 600 and 610, respectively, enhances the likelihood that transdermal transport and/or activation of the drug is achieved.

In still another aspect of the present method, beam 610 is used to induce cavitation in fluid-containing organs or tissue, either with or without associated imaging with beam 600. Cavitation has been shown to ablate tissue in the gallbladder and prostate. The ability to simultaneously image the structure undergoing cavitation-induced tissue therapy enhances greatly the efficacy of the therapy.

Insofar as the ultrasonic signal frequency and intensity at which cavitation is induced varies with the medium, specific frequencies and intensities cannot be given. However, once the appropriate frequency, intensity and other factors are selected, which selection is within the ability of one skilled in the art, such information is input via user controls 14 to system 6. Then, as described above, beam 610 is generated and delivered to portion 604 where cavitation therapy is desired.

Other methods of ultrasonic application not described above involving function provided by system 6 not previously available are also encompassed by the present invention. Thus, since certain changes may be made in the above system and processes without departing from the scope of the invention described herein, it is intended that all matter contained in the above description or shown in the accompanying drawings shall be interpreted in an illustrative and not in a limiting sense.

What is claimed is:

1. An ultrasonic imaging system comprising:

a. a source for providing a first signal; and b. a transducer array connected to said source for providing ultrasonic energy in response to said first signal, wherein said ultrasonic energy has a resonant frequency greater than 5 MHz and said transducer array has a plurality of multilayer transducer elements, each having an electrical impedance of less than 100 Ohms.

2. An ultrasonic imaging system according to claim 1, wherein said ultrasonic energy has a frequency greater than 15 MHz and said transducer array has an electrical impedance of less than 100 Ohms.

3. A system according to claim 1, wherein said transducer array provides an output signal in response to receipt of ultrasonic energy reflected off a target, said output signal containing information regarding the configuration of said target, the system further comprising:

c. display means connected to said transducer array for providing a representation of features of said target based on said information in said output signal.

4. A system according to claim 1, wherein said transducer array has a plurality of transducer elements, each having height, width and length dimensions, wherein said length dimension is no more than five times said width dimension.

5. A system according to claim 4, wherein said width dimension is equal to half said height dimension.

6. A ultrasonic imaging system comprising:

a. a source for providing first and second signals; and b. a transducer array connected to said source, said array including:

i. a plurality of first multilayer transducer elements for providing ultrasonic energy at a first resonant frequency in response to said first signal; and ii. a plurality of second multilayer transducer elements for providing ultrasonic energy at a second resonant frequency in response to said second signal; and c. wherein said plurality of first transducer elements is acoustically isolated from said plurality of second transducer elements.

7. A system according to claim 6, wherein said transducer array provides a third signal in response to receipt of ultrasonic energy reflected off a target, the system further comprising:

c. a processor connected to said transducer array for providing an image signal based on information contained in said third signal; and d. image depiction means connected to said processor for providing a representation of said target based on information contained in said image signal.

8. A system according to claim 7, wherein said image depiction means is a visual display device.

9. A system according to claim 6, wherein said first and second resonant frequencies are spaced by more than 15 MHz.

10. A system according to claim 6, wherein said first resonant frequency is less than 0.3 times the average of said first and second frequencies and said second resonant frequency is more than 1.7 times the average of said first and second frequencies.

11. An ultrasonic imaging system comprising:

a. a source for providing a first signal having an electrical impedance of less than 100 Ohms; and b. a transducer array connected to said source for providing ultrasonic energy in response to said first signal, said transducer array having at least two transducer elements, a resonant frequency greater than 5 MHz and an electrical impedance that substantially matches said electrical impedance of said source.

12. A system according to claim 11, wherein said resonant frequency is greater than 10 MHz.

13. An ultrasonic imaging system comprising:

a. a source for providing drive signals; and b. a transducer array connected to said source for providing ultrasonic energy in response to said drive signals, wherein said array includes a plurality of elements, at least one of which has a single layer of piezoelectric material and at least one of which has a plurality of layers of piezoelectric material, further wherein at least one of said elements has a resonant frequency of more than 10 MHz.

14. A system according to claim 13, wherein at least one of said elements has a resonant frequency of more than 15 MHz.

15. A system according to claim 13, wherein said piezoelectric material is PZT.

16. A system according to claim 13, wherein said elements having a plurality of layers of piezoelectric material provide said ultrasonic energy, further wherein said elements having a single layer of piezoelectric material provide an output signal in response to receipt of ultrasonic energy.

17. An ultrasonic imaging system comprising:

a. a source for providing a first signal; and b. a transducer array connected to said source for providing ultrasonic energy in response to said first signal, further wherein said array has a plurality of multilayer transducer elements, each having a height, width and length dimension, wherein at least one of said width and length dimensions is less than 50 microns.

18. A system according to claim 17, wherein at least one of said width and length dimensions does not exceed 25 microns.

19. An ultrasonic imaging system comprising:

a. a source for providing a first signal; and b. a transducer array connected to said source, said array having:

i. a plurality of elements, each for providing ultrasonic energy in response to said first signal;

ii. a plurality of element regions, each of which may contain a corresponding respective one of said plurality of elements; and iii. wherein at least one of said plurality of element regions does not contain one of said plurality of elements.

20. A system according to claim 19, wherein said transducer array has X element regions and Y elements, wherein the ratio of X/Y is 0.75 or less.

21. A system according to claim 20, wherein said ratio is 0.25 or less.

22. An ultrasonic imaging system comprising:

c. a source for providing a first signal; and d. a transducer array connected to said source, said array having a plurality of elements for providing ultrasonic energy in response to said first signal, each having a length, width and height, wherein said length is no more than 5 times said width, further wherein at least one of said elements provides said ultrasonic energy at a frequency greater than 10 MHz.

23. A system according to claim 22, wherein said length is about equal to said width.

24. A system according to claim 22, wherein said array is a 2-D array.

25. A system according to claim 22, wherein said array is a 1.5-D array.

26. A system according to claim 22, wherein said array is a 1-D array.

27. An ultrasonic imaging system comprising:

a. a beamformer for providing a first signal;

b. a processor connected to said beamformer;

c. a probe connected to said beamformer, said probe having an ultrasonic transducer array having a plurality of transducer elements, at least one of which elements has multiple layers of piezoelectric material and an electrical impedance of less than 100 Ohms, wherein said at least one element provides ultrasonic energy having a frequency of more than 5 MHz in response to said first signal;

d. user controls connected to said processor; and e. a display connected to said processor.

28. A system according to claim 27, wherein said ultrasonic energy has a frequency of more than 10 MHz.

29. A method of administering ultrasound comprising the steps of:

a. providing an ultrasound transducer array including:

i. a plurality of first transducer elements for providing a first ultrasound signal, said plurality of first transducer elements each having a first resonant frequency;

ii. a plurality of second transducer elements for providing a second ultrasound signal, said plurality of second resonant frequency that is different than said first resonant frequency;

iii. wherein at least one of said plurality of first transducer elements and/or said plurality of second transducer elements has more than one layer of piezoelectric material:

b. providing said first ultrasound signal from said transducer array;

c. providing said second ultrasound signal from said transducer array; and d. wherein one of said first and second resonant frequencies is greater than 10 MHz.

30. A method according to claim 29, wherein one of said first and second resonant frequencies is greater than 15 MHz.

31. A method according to claim 29, wherein one of said first and second resonant frequencies is greater than 20 MHz.

32. A method according to claim 29, wherein said first resonant frequency differs by at least 15 MHz from said second resonant frequency.

33. A method according to claim 29, wherein said first resonant frequency is less than 0.3 times the average of said first and second resonant frequencies and said second resonant frequency is more than 1.7 times the average of said first and second resonant frequencies.

34. A method according to claim 29, wherein said second resonant frequency is higher than said first resonant frequency.

35. A method according to claim 29, wherein said step b involves providing said first ultrasound signal so as to intercept a section of a body.

36. A method according to claim 35, wherein said step c involves providing said second ultrasound signal at a frequency causing cavitation in said section of said body.

37. A method according to claim 35, further comprising the step, prior to said step a, of providing to said section of said body a therapeutic agent that changes state when exposed to ultrasound energy having a frequency equal to the resonant frequency of one of said first and second ultrasound signals.

38. A method according to claim 35, further comprising the step, prior to said step a, of providing to said section of said body a therapeutic agent, the transdermal transport of which is enhanced when exposed to ultrasound energy having a frequency equal to the frequency of said second ultrasound signal.

39. A method according to claim 35, further wherein said step b involves forming and steering said second ultrasound signal relative to said section of said body so as to provide treatment to tissue in said section.

40. A method according to claim 39, wherein said treatment is ablation of said tissue.

41. A method according to claim 39, wherein said treatment is incision of said tissue.

42. A method according to claim 39, wherein said treatment is heating of said tissue.

43. A method of administering ultrasound comprising the steps of:

a. providing an ultrasound transducer array proximate a target, said array including:

i. a plurality of first transducer elements for providing a first ultrasound signal, said plurality of first transducer elements each having a first resonant frequency;

ii. a plurality of second transducer elements for receiving a second ultrasound signal, said plurality of second transducer each having a second resonant frequency that is different than said first resonant frequency;

b. providing said first ultrasound signal from said transducer array so as to intercept and reflect off said target thereby forming said second ultrasound signal;

c. receiving said second ultrasound signal with said transducer array; and d. wherein one of said first and second resonant frequencies is greater than 10 MHz.

44. A method according to claim 43, further comprising the step, prior to said step a, of adding a contrast agent to said section that reflects ultrasound energy in a harmonic of one of said first and second resonant frequencies.

45. A method according to claim 43, wherein one of said first and second resonant frequencies is greater than 15 Mhz.

46. A method according to claim 43, said second ultrasound signal containing information regarding the configuration of a target, the method further comprising the steps of:

e. providing a first signal with said ultrasound transducer array following receipt of said second ultrasound signal; and f. generating a representation of the target based the information contained in said second ultrasonic signal.

47. A method according to claim 46, wherein said representation is three dimensional.

48. A method of ultrasonic imaging comprising the steps of:

a. generating a drive signal having an electrical impedance of less than 100 Ohms and a frequency of more than 5 MHz;

b. providing said drive signal to an ultrasonic transducer array having one or more multilayer transducer elements with an electrical impedance of less than 100 Ohms and a resonant frequency of more than 5 MHz; and c. providing ultrasonic energy with said ultrasonic transducer in response to said drive signal.

49. A method according to claim 48, wherein said step a involves generating said drive signal at a frequency of more than 10 MHz and said step b involves providing said drive signal to an ultrasonic transducer array having a resonant frequency of more than 10 MHz.

50. A system according to claim 1, wherein said transducer array has an axis and said plurality of multilayer transducer elements are positioned to surround said axis.

51. A system according to claim 50, wherein at least one of said plurality of multilayer transducer elements is curved.

52. A system according to claim 6, wherein said transducer array has an axis and said plurality of multilayer transducer elements are positioned to surround said axis.

53. A system according to claim 52, wherein at least one of said plurality of multilayer transducer elements is curved.

54. A system according to claim 13, wherein said transducer array has an axis and said plurality of multilayer transducer elements are positioned to surround said axis.

55. A system according to claim 54, wherein at least one of said plurality of multilayer transducer elements is curved.

56. A system according to claim 27, wherein said transducer array has an axis and said plurality of multilayer transducer elements are positioned to surround said axis.

57. A system according to claim 56, wherein at least one of said plurality of multilayer transducer elements is curved.

58. A system according to claim 1, wherein at least one of said plurality of multilayer transducer elements has a layer of PZT.

59. An ultrasonic imaging system comprising:

a. a source for providing first and second signals; and b. a transducer array connected to said source, said array including:

i. a plurality of first transducer elements for providing ultrasonic energy at a first resonant frequency in response to said first signal; and ii. a plurality of second transducer elements for providing ultrasonic energy at a second resonant frequency in response to said second signal; and c. wherein said plurality of first transducer elements is acoustically isolated from said plurality of second transducer elements and wherein said first and second resonant frequencies are spaced by more than 15 MHz.

60. An ultrasonic imaging system comprising:

a. a source for providing first and second signals; and b. a transducer array connected to said source, said array including:

i. a plurality of first transducer elements for providing ultrasonic energy at a first resonant frequency in response to said first signal; and ii. a plurality of second transducer elements for providing ultrasonic energy at a second resonant frequency in response to said second signal; and c. wherein said plurality of first transducer elements is acoustically isolated from said plurality of second transducer elements and wherein said first resonant frequency is less than 0.3 times the average of said first and second frequencies and said second resonant frequency is more than 1.7 times the average of said first and second frequencies.

* * * * *